(12) United States Patent
Kietzmann et al.

(10) Patent No.: US 11,103,633 B2
(45) Date of Patent: Aug. 31, 2021

(54) PACKAGING ASSEMBLY WITH MOUNTING ATTACHMENT

(71) Applicant: Sanofi-Aventis Deutschland GMBH, Frankfurt am Main (DE)

(72) Inventors: Hardy Kietzmann, Frankfurt am Main (DE); Fred Luck, Frankfurt am Main (DE); Stefan Riebel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 93 days.

(21) Appl. No.: 15/779,747

(22) PCT Filed: Nov. 28, 2016

(86) PCT No.: PCT/EP2016/079039
§ 371 (c)(1),
(2) Date: May 29, 2018

(87) PCT Pub. No.: WO2017/093199
PCT Pub. Date: Jun. 8, 2017

(65) Prior Publication Data
US 2020/0054820 A1 Feb. 20, 2020

(30) Foreign Application Priority Data
Nov. 30, 2015 (EP) .................................. 15197096

(51) Int. Cl.
*B65D 83/10* (2006.01)
*B65D 85/20* (2006.01)
(Continued)

(52) U.S. Cl.
CPC ............ *A61M 5/002* (2013.01); *A61M 5/008* (2013.01); *B65D 83/10* (2013.01); *B65D 85/20* (2013.01);
(Continued)

(58) Field of Classification Search
CPC ... A45C 2011/007; A61M 5/00; A61M 5/002; A61M 5/008; A61M 2209/082; B65D 83/10; B65D 85/20; B65D 25/22
(Continued)

(56) References Cited

U.S. PATENT DOCUMENTS 2,698,155 A 12/1954 Bowman
4,572,403 A 2/1986 Benaroya
(Continued)

FOREIGN PATENT DOCUMENTS

CN 2568179 8/2003
CN 1630604 6/2005
(Continued)

OTHER PUBLICATIONS

International Preliminary Report on Patentability in International Application No. PCT/EP2016/079039, dated Jun. 5, 2018, 7 pages.
(Continued)

*Primary Examiner* — Bryon P Gehman
(74) *Attorney, Agent, or Firm* — Fish & Richardson P.C.

(57) ABSTRACT

A packaging assembly includes a case configured to hold at least one injection device for delivering a medicament and a mounting attachment configured to be attached to the case. The case includes one or more magnets for attaching the mounting attachment to the case and an external face of the case is formed having a recess configured to receive at least part of the mounting attachment.

15 Claims, 7 Drawing Sheets

(51) Int. Cl.
*A45C 11/00* (2006.01)
*A61M 5/00* (2006.01)

(52) U.S. Cl.
CPC .. *A45C 2011/007* (2013.01); *A61M 2209/082* (2013.01)

(58) Field of Classification Search
USPC ................................................ 206/364, 366
See application file for complete search history.

(56) References Cited

U.S. PATENT DOCUMENTS

| | | | |
|---|---|---|---|
| 4,903,832 A * | 2/1990 | Stewart | A61B 50/36 206/366 |
| 5,522,503 A | 6/1996 | Halbich | |
| 5,915,558 A | 6/1999 | Girvetz | |
| 5,970,974 A | 10/1999 | Van der Linden et al. | |
| 6,056,118 A | 5/2000 | Hargus et al. | |
| 6,464,506 B1 | 10/2002 | Dickerson | |
| 6,595,362 B2 * | 7/2003 | Penney | A61M 5/002 206/364 |
| 6,955,259 B1 * | 10/2005 | Jesse | A61M 5/008 206/366 |
| 7,434,686 B2 * | 10/2008 | Prindle | A61M 5/002 206/364 |
| 8,544,645 B2 | 10/2013 | Edwards et al. | |
| 8,584,486 B1 | 11/2013 | Allard et al. | |
| 9,311,452 B2 | 4/2016 | Dickie et al. | |
| 2002/0050462 A1 | 5/2002 | Penney et al. | |
| 2004/0069667 A1 | 4/2004 | Tomellini et al. | |
| 2007/0214812 A1 | 9/2007 | Wagner et al. | |
| 2007/0215782 A1 * | 9/2007 | Phung | A61G 7/0503 248/691 |
| 2009/0115598 A1 | 5/2009 | Carlson | |
| 2009/0134181 A1 | 5/2009 | Wachman et al. | |
| 2012/0232520 A1 | 9/2012 | Sloan et al. | |
| 2013/0002795 A1 | 1/2013 | Shavelsky et al. | |
| 2013/0289536 A1 | 10/2013 | Croizat et al. | |
| 2014/0252927 A1 | 9/2014 | Denny et al. | |
| 2015/0048100 A1 | 2/2015 | Dickie et al. | |
| 2015/0283341 A1 | 10/2015 | Adams et al. | |
| 2015/0317455 A1 | 11/2015 | Lehmann et al. | |
| 2015/0378314 A1 | 12/2015 | Nakabayashi | |
| 2016/0129182 A1 | 5/2016 | Schuster et al. | |
| 2016/0162832 A1 | 6/2016 | Thompson et al. | |
| 2016/0199592 A1 | 7/2016 | Eggert et al. | |
| 2016/0232877 A1 | 8/2016 | Cho et al. | |
| 2016/0243318 A1 | 8/2016 | Despa et al. | |
| 2017/0056605 A1 | 3/2017 | Kondo et al. | |
| 2017/0087059 A1 | 3/2017 | Rodriguez et al. | |
| 2017/0368260 A1 | 12/2017 | McCullough et al. | |

FOREIGN PATENT DOCUMENTS

| | | |
|---|---|---|
| CN | 2744339 | 12/2005 |
| CN | 101073533 | 11/2007 |
| CN | 101384237 | 3/2009 |
| CN | 201352126 | 11/2009 |
| CN | 201664175 | 12/2010 |
| CN | 201877103 | 6/2011 |
| CN | 102542176 | 7/2012 |
| CN | 202287671 | 7/2012 |
| CN | 202311770 | 7/2012 |
| CN | 202426229 | 9/2012 |
| CN | 203634510 | 6/2014 |
| CN | 104055678 | 9/2014 |
| CN | 203970030 | 12/2014 |
| CN | 204050542 | 12/2014 |
| CN | 204351461 | 5/2015 |
| CN | 204467263 | 7/2015 |
| CN | 204766326 | 11/2015 |
| CN | 204890775 | 12/2015 |
| DE | 20201026 | 4/2002 |
| DE | 10132869 | 10/2002 |
| EP | 2119423 | 11/2009 |
| EP | 3010660 | 4/2016 |
| EP | 3103493 | 12/2016 |
| EP | 3449575 | 3/2019 |
| GB | 2520054 | 5/2015 |
| JP | S51-93401 | 7/1976 |
| JP | 2002-504397 | 2/2002 |
| JP | 2008-114008 | 5/2008 |
| KR | 10-1564249 | 11/2015 |
| WO | WO 1999/043283 | 9/1999 |
| WO | WO 01/87739 | 11/2001 |
| WO | WO 2003/062091 | 7/2003 |
| WO | WO 2005/046559 | 5/2005 |
| WO | WO 2007/082543 | 7/2007 |
| WO | WO 2007/126851 | 11/2007 |
| WO | WO 2011/054000 | 5/2011 |
| WO | WO 2011/070329 | 6/2011 |
| WO | WO 2013/025520 | 2/2013 |
| WO | WO 2013/050342 | 4/2013 |
| WO | WO 2014/096146 | 6/2014 |
| WO | WO 2014/159933 | 10/2014 |
| WO | WO 2014/192888 | 12/2014 |
| WO | WO 2014/204958 | 12/2014 |
| WO | WO 2015/032715 | 3/2015 |
| WO | WO 2015/151900 | 10/2015 |
| WO | WO 2016/022760 | 2/2016 |
| WO | WO 2016/142726 | 9/2016 |
| WO | WO 2017/186402 | 11/2017 |
| WO | WO 2018/153945 | 8/2018 |
| WO | WO 2018/154033 | 8/2018 |
| WO | WO 2018/172858 | 9/2018 |

OTHER PUBLICATIONS

International Search Report and Written Opinion in International Application No. PCT/EP2016/079039, dated Feb. 21, 2017, 9 pages.
PCT International Preliminary Report on Patentability in International Appln. No. PCT/EP2016/079038, dated Jun. 5, 2018, 7 pages.
PCT International Preliminary Report on Patentability in International Appln. No. PCT/EP2016/079040, dated Jun. 5, 2018, 6 pages.
PCT International Search Report and Written Opinion in International Appln. No. PCT/EP2016/079038, dated Feb. 17, 2017, 10 pages.
PCT International Search Report and Written Opinion in International Appln. No. PCT/EP2016/079040, dated Feb. 6, 2017, 8 pages.
PCT International Preliminary Report on Patentability in International Appln. No. PCT/EP2018/054464, dated Aug. 27, 2019, 7 pages.
PCT International Search Report and Written Opinion in International Appln. No. PCT/EP2018/054464, dated May 23, 2018, 10 pages.
PCT International Preliminary Report on Patentability in International Appln. No. PCT/EP2018/054323, dated Aug. 27, 2019, 7 pages.
PCT International Search Report and Written Opinion in International Appln. No. PCT/EP2018/054323, dated May 4, 2018, 11 pages.

* cited by examiner

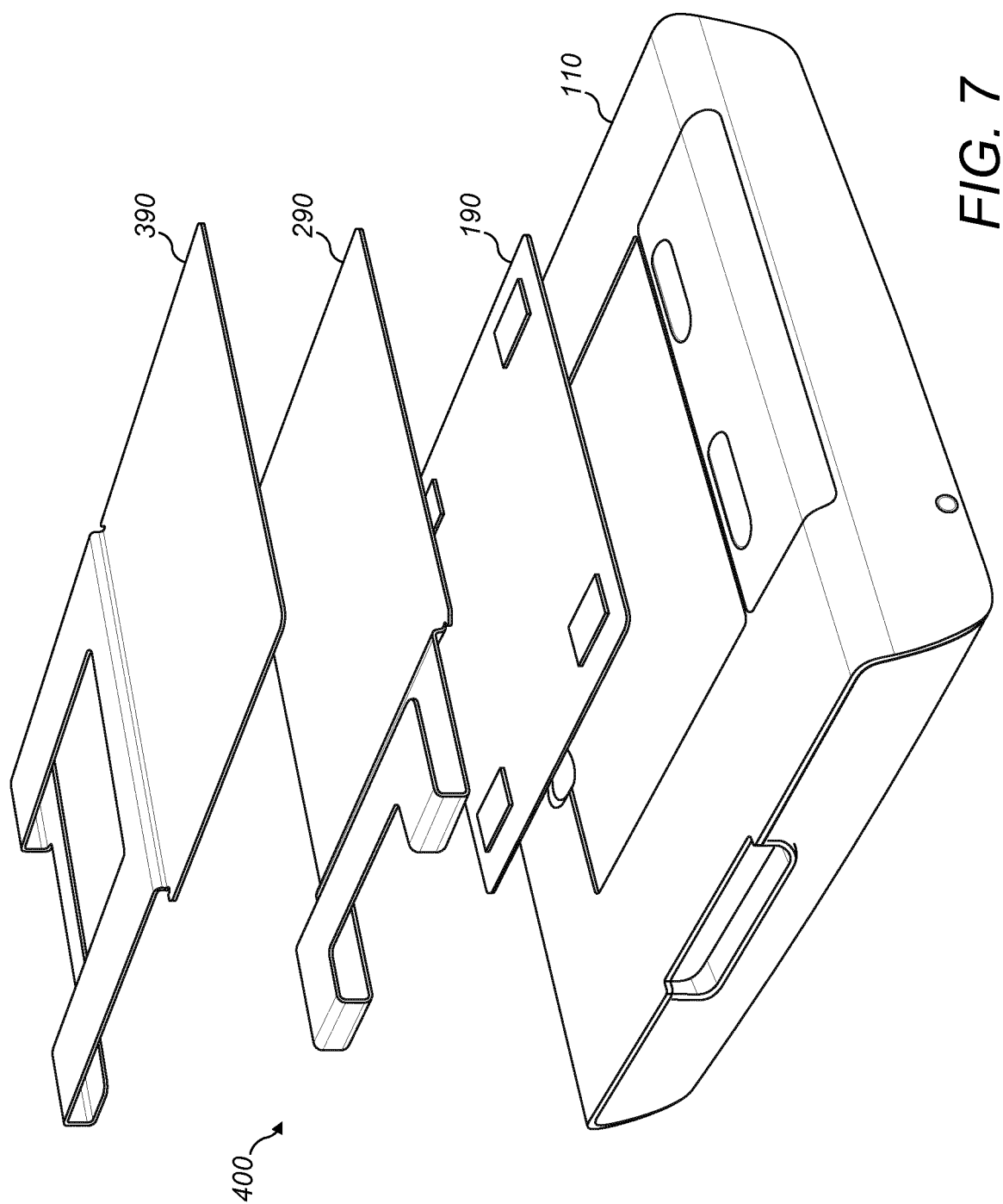

PACKAGING ASSEMBLY WITH MOUNTING ATTACHMENT

CROSS REFERENCE TO RELATED APPLICATIONS

The present application is the national stage entry of International Patent Application No. PCT/EP2016/079039, filed on Nov. 28, 2016, and claims priority to Application No. EP 15197096.9, filed on Nov. 30, 2015, the disclosures of which are expressly incorporated herein in entirety by reference thereto.

TECHNICAL FIELD

The disclosure relates to a packaging assembly for a medicament.

BACKGROUND

Patients suffering chronic disease require regular treatment with medicaments, e.g. on the basis of a predefined schedule. Particular medicaments require refrigerated storage, and are often stored refrigerated in a household refrigerator or fridge. In a home treatment environment, the patient stores the medicament in their own fridge and administers a predefined dose as required. Hence, the medicament is typically provided in a secondary packaging for convenient placement and storage in the household fridge. However, the medicament must be stored together with other items that require constant refrigeration, like foodstuffs and beverages.

Depending on the dosage form of the medicament, the secondary packaging containing the medicament may store a primary packed medicament itself, or may store one or more different kinds of drug delivery devices. For instance, the medicament may be provided in a pre-filled syringe or pen-type injector.

A medicament may have a predefined dosing schedule which requires the administration of a dose at relatively long intervals, for instance every two weeks, or once a month. The medicament may be provided in a secondary packaging containing several doses which may be stored in the fridge for 3 or 6 months for instance. It can be difficult for patients to keep track of each scheduled dosing time.

SUMMARY

According to an embodiment of the disclosure, a packaging assembly is provided including a case configured to hold at least one injection device for delivering a medicament; and a mounting attachment configured to be attached to the case; wherein the case comprises one or more magnets for attaching the mounting attachment to the case, and an external face of the case is formed having a recess configured to receive at least part of the mounting attachment.

The one or more magnets may be arranged on an internal face of the case, and the one or more magnets may be arranged in alignment with the recess.

The case may include a plurality of internal walls configured to maintain the arrangement of the one or more magnets, wherein each of the one or more magnets is held between at least two of the internal walls.

The mounting attachment may include a rectangular mounting plate, wherein the recess is configured to receive at least part of the mounting plate when the mounting attachment is attached to the case.

The depth of the recess may be equal to the thickness of the mounting plate.

At least a portion of the mounting plate may include an adhesive layer.

The mounting attachment may include a hanger arrangement; wherein the hanger arrangement extends from the mounting plate and comprises a hook at an end furthest from the mounting plate.

The hook may be disposed towards the case when the mounting attachment is attached to the case.

The hook may be disposed away from the case when the mounting attachment is attached to the case.

According to another aspect, a packaging assembly is provided including a case configured to hold at least one injection device for delivering a medicament; and a mounting attachment configured to be attached to the case; wherein the mounting attachment comprises a hanger arrangement which extends from the case substantially in the plane of an external face of the case when the mounting attachment is attached to the case, and the hanger arrangement comprises a hook at an end furthest from the case wherein the hook is fixed in position extending out of the plane of the external face of the case and disposed towards the case when the mounting attachment is attached to the case.

The mounting attachment may be formed as part of the case.

The mounting attachment may include a rectangular mounting plate configured to be attached to the external face of the case, wherein the hanger arrangement is arranged to extend from the mounting plate.

The case may include one or more magnets for attaching the mounting attachment to the case.

The external face of the case may be formed having a recess to receive at least part of the mounting plate when the mounting attachment is attached to the case.

According to another aspect, a kit for providing a packaging assembly in provided including a case configured to hold at least one injection device for delivering a medicament, which comprises one or more magnets for attaching the case to a mounting attachment; a first mounting attachment comprising a rectangular mounting plate, wherein at least a portion of the mounting plate comprises an adhesive layer; a second mounting attachment comprising a mounting plate and a hanger arrangement, wherein the hanger arrangement comprises a hook at an end furthest from the case and the hook is disposed towards the case when the second mounting attachment is attached to the case; and a third mounting attachment comprising a mounting plate and a hanger arrangement, wherein the hanger arrangement comprises a hook at an end furthest from the case and the hook is disposed towards away from the case when the third mounting attachment is attached to the case.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which:

FIG. 7 is an isometric view of a kit according to an exemplary embodiment.

DETAILED DESCRIPTION

Figure 1:
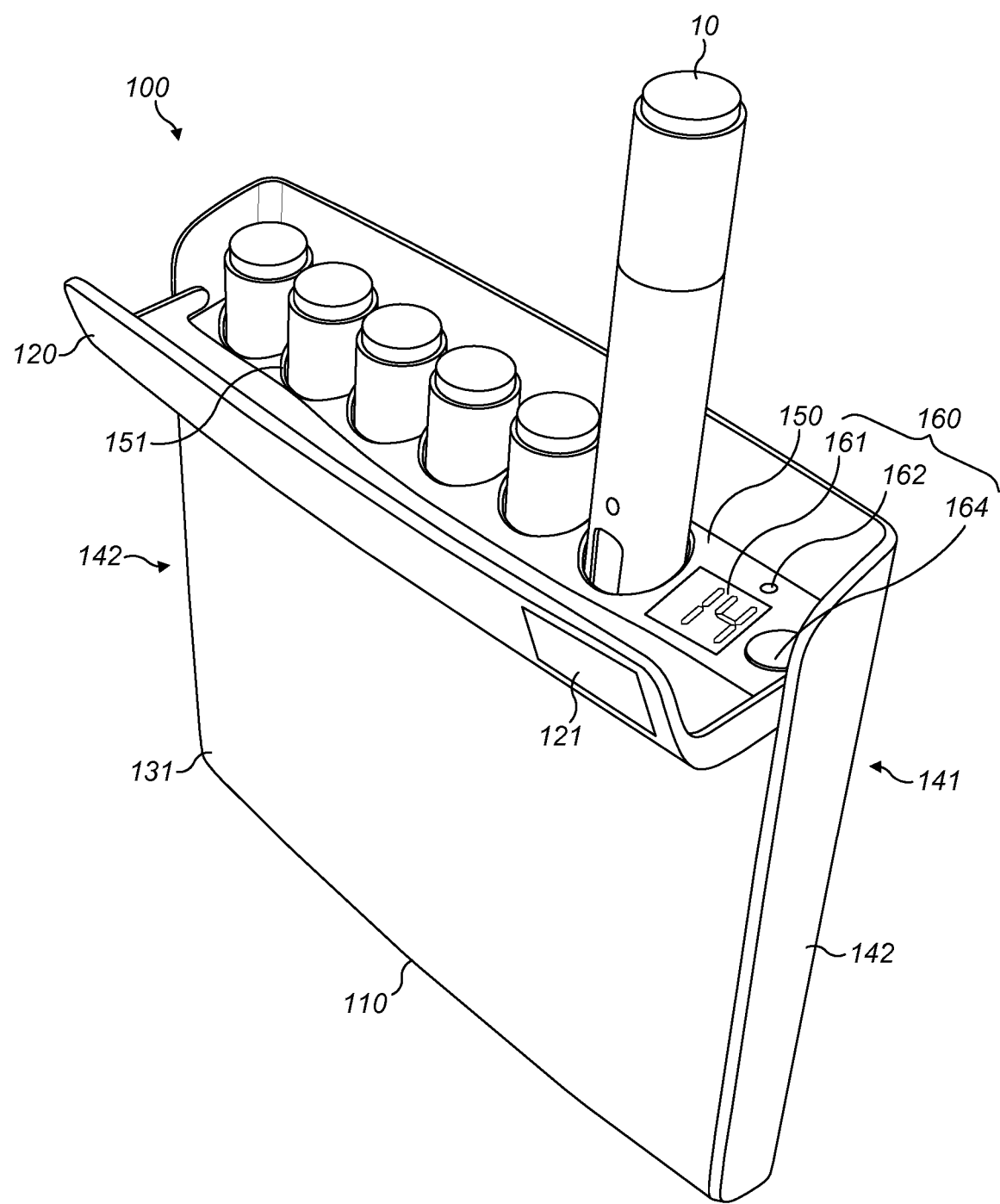
FIG. 1 is an isometric view of a packaging assembly according to a first exemplary embodiment.

Embodiments of the disclosure provide a packaging assembly configured to contain and store a plurality of injection devices for delivering a medicament. An injection device is an example of a drug delivery device and may be a pen-injector or an auto-injector. The packaging assembly may be stored in a household refrigerator or fridge.

The patient may receive the packaging assembly in an empty condition. When the patient is supplied with a plurality of injection devices they can be loaded into the packaging assembly. The packaging assembly may be placed in the fridge until a scheduled dosing time is due.

The packaging assembly may include a mounting arrangement to allow a patient to locate the packaging assembly in various positions in their fridge. For example, the packaging assembly may be located for convenient access to make it easier for a patient to be reminded that an injection is due. Depending on the patient's needs, the assembly may be positioned discreetly in the fridge (e.g. to keep the assembly from children), or positioned prominently within the fridge to serve as a constant reminder when they open their fridge door. The packaging assembly may be positioned prominently within the fridge. The packaging assembly may be conveniently positioned out of the way of food in the fridge, in an accessible position. The assembly may also be moved if the patient desires, or temporarily removed for periodic cleaning. Various assembly embodiments and uses are described below.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml.

Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

With reference to FIGS. 1 to 4, a packaging assembly 100 according to exemplary embodiments is shown. The packaging assembly 100 comprises a case 110 having a lid 120. The case 110 comprises a front wall 130, a rear wall 141, and two side walls 142. The front wall 131 is curved so as to meet the rear wall 141 at a base of the device. At an upper end of the case 110, an opening is formed between front wall 131, the rear wall 141 and the two side walls 142.

The lid 120 of the case 110 is arranged to cover the opening of the case 110. The lid 120 is attached between the two side walls 142 of the case 110 in a hinged manner. The lid 120 can be freely moved in a hinged manner between a closed position and an open position. In the closed position, the lid 120 is arranged to cover the opening of the case 110. In the open position, the opening of the case 110 is uncovered and an interior of the case 110 can be accessed.

The lid 120 may comprise a latching mechanism to hold the lid 120 in the closed position. The latching mechanism may comprise a protruding part arranged at an edge of the lid 120. The protruding part may be configured to engage with a corresponding feature in the case 110 when the lid is in the closed position. The protruding part may be flexible or retractable to disengage from the case 110 and allow the lid 120 to move to the open position.

The case 110 is configured to hold and store a plurality of injection devices. A height of the case 110, measured between the base and the lid 120, is sufficient to accommodate the length of each of the injection devices. The height of the case may be between about 160 mm and about 180 mm. A depth of the case 110, measured between the front wall 131 and the rear wall 141, is sufficient to accommodate the width of each of the injection devices. The depth of the case may be between about 30 mm and about 40 mm. A width of the case 110, measured between the two side walls 142, is sufficient to accommodate six injection devices. The width of the case may be between about 180 mm and about 200 mm.

As shown in FIG. 1, the front wall 131 of the case 110 is shorter than the rear wall 141. The lid 120 extends from a top edge of the front wall 131 to a top edge of the rear wall 141. The lid 120 is curved. The curve allows the lid 120 to form the top and a portion of the front of the case 110 in the closed position. Other lid configurations are also contemplated.

The front wall 131, the rear wall 141 and the two side walls 142 are formed from an opaque material, for example, an opaque plastic material. The lid 120 is formed from a translucent or frosted material, for example, a clear plastic material with a frosted coating or a treated surface. A portion of the lid 120 is clear and transparent to form a viewing window 121 through the lid 120.

The case 110 further comprises a panel 150 arranged within the opening. The panel 150 is fully visible only when the lid 120 of the case 110 is in an open position; when the lid 120 is in the closed position, the lid at least partially obscures the panel 150 from view. The panel 150 comprises a plurality of openings 151. The openings 151 are configured to hold a corresponding plurality of injection devices. The openings 151 in the panel 150 are circular in shape. The openings 151 may be square shaped, or rectangular shaped to accommodate other sizes of injection device. The width of each opening is sufficient to accommodate the width of each injection device. The panel 150 comprises a row of six openings, so as to hold six injection devices arranged in a row along a width of the case 110. The packaging assembly 100 may be configured to hold more than six, or fewer than six injection devices in the case 110.

The lid 120 may be configured to retain the plurality of injection devices in position within the case 110 when in the closed position. The lid 120 can be moved into the open position and each of the injection devices is inserted into a corresponding one of the openings 151. The lid 120 may be moved into the closed position to prevent the injection devices from falling or sliding out of the case 110. Each injection device may be retained in position within the corresponding opening 151 by a friction fit with the opening 151.

A retention mechanism may retain the plurality of injection devices in position within the openings 151. The retention mechanism may comprise a mechanical catch configured to engage with each injection device, for example, a sprung push-catch push-release mechanism. The injection device is pushed into the opening 151 and pushed against a spring of the retention mechanism to engage a catch. The injection device is pushed a second time to release the catch. A release button or switch (not shown) may be provided for each of the openings 151, which is configured to release the catch of the retention mechanism when pressed.

The packaging assembly 100 may be configured to provide the patient with a visual and/or reminder when the scheduled dosing time is due. The packaging assembly 100 includes an electronics system 160. The electronics system 160 comprises multiple components that are connected together to provide a specific set of functions. The components of the electronics system 160 are mounted on a printed circuit board (PCB), although instead they may be interconnected through some other medium.

The electronics system 160 is attached to the panel 150. Some of the electronic components of the electronics system 160 are user interface hardware components and together provide a user interface. The components that provide the user interface are positioned at one end of the row of openings 151 of the panel 150.

The electronics system 160 comprises a display 161. The display 161 is an example of an optical transducer. The display 161 comprises two seven-segment light-emitting diode (LED) arrays. The display 161 is visible to the user through the transparent viewing window 121 in the lid 120. The electronics system 160 comprises a light-emitting diode (LED) 162. The LED 162 is an example of an optical transducer. A colour of the LED 162 is different to a colour of the seven-segment LED arrays in the display 161, for example, the colour of the LED 162 is red and the colour of the display 161 is blue. The electronics system 160 comprises a reset button 164. The reset button 164 is an example of an input device. The reset button 164 is a sprung plunger button which may be depressed by the user. The electronics system 160 may further comprise a speaker (not shown). The speaker is an example of an audio transducer.

The electronics system 160 further comprises a processor arrangement (not shown). The processor arrangement may be configured to control the outputs of the user interface elements on the electronics system 160. The processor arrangement may be configured to monitor a time remaining until a scheduled dosing time is due. The processor arrangement may operate any of the display 161, the LED 162 and the speaker to provide an output when the scheduled dosing time is due. The processor arrangement may be configured to reset the time remaining until the scheduled dosing time is due in response to an input from the reset button 164.

Figure 2:
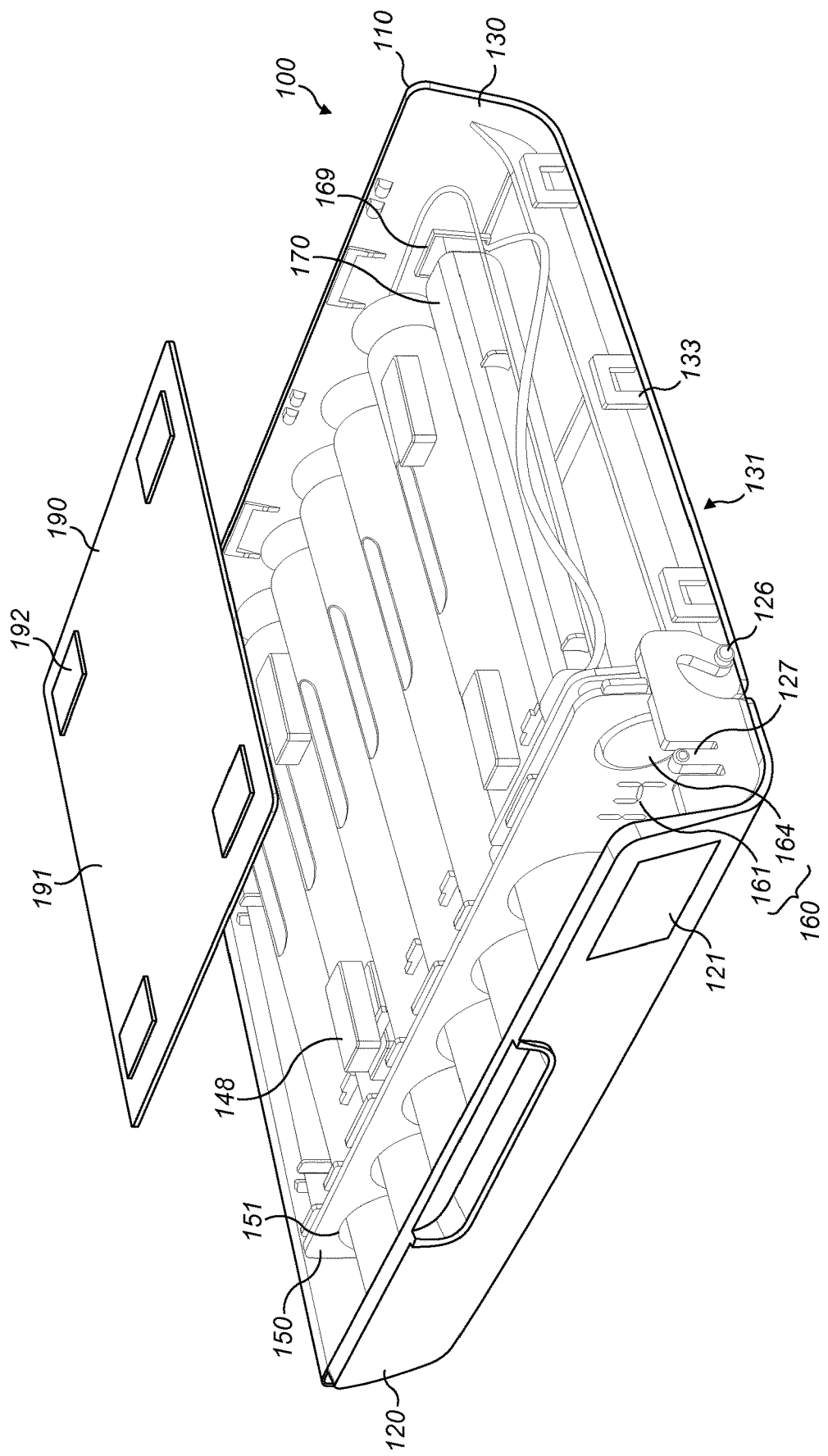
FIG. 2 is an isometric view of the packaging assembly of FIG. 1.

With further reference to FIG. 2, a cross-section view of the packaging assembly 100 is shown. The case 110 of the packaging assembly 100 comprises a first part 130 and a second part 140. The second part 140 is omitted from FIG. 2 to show an interior of the case 110.

The first part 130 of the case 110 comprises the front wall 131 and the base of the packaging assembly 100. The first part 130 of the case 110 is formed from a single piece. Along each side edge of the front face 131, a plurality of openings 133 are formed for engaging with the second part 140 of the case 110. Three openings 133 are formed along each edge of the first part 130.

The first part 130 further comprises a plurality of guide rails 134 for holding the plurality of injection devices in position within the case 110. The guide rails 134 are internal walls which extend along the length of the case 110 from the openings 151 to the base of the first part 130. Three guide rails 134 are provided for each of the openings 151. For each set of three guide rails 134, the two outer rails are taller than the central rail.

The lid 120 of the case 110 comprises a first hinging part 126. The first hinging part 126 comprises a protruding part configured to engage with a corresponding feature in the second part 140. The lid 120 is configured to pivot about the first hinging part 126 to move between the closed position and the open position.

The lid 120 of the case 110 comprises a first latching part 127. The first latching part 127 comprises a protruding part configured to engage with a corresponding feature in the second part 140 and maintain the lid 120 in the closed position. The first latching part 127 may be flexible or retractable to disengage from the second part 140 and allow the lid 120 to move to the open position.

The panel 150 is held in position between the first part 130 and the second part 140 of the case 110. Alternatively, the panel is integrally formed with the first part 130. A support of the electronics system 160, for instance a PCB, is attached to a rear face of the panel 150.

The packaging assembly 100 comprises a plurality of batteries 170. The batteries 170 are arranged to provide power to the components of the user interface. The batteries 170 are coupled to the electronics system 160 with a battery contact 169. The battery contact 169 is mounted with the plurality of batteries 170 in order to supply power to the electronics system 160.

The case 110 of the packaging assembly 100 comprises a plurality of magnets 148. The magnets 148 are fixed in position on an internal side of the rear wall 141. The case 110 comprises four magnets 148 fixed in a square arrangement. The plurality of magnets 148 allows the rear wall 141 of the case 110 to be releasably attached to a magnetic surface, for example, a steel surface. The magnets 148 may be neodymium magnets.

The packaging assembly 100 further comprises a mounting attachment 190. The mounting attachment 190 comprises a mounting plate 191. The mounting plate 191 is formed from a magnetic material, for example, steel. The mounting plate 191 can be releasably attached to the case 110 using the plurality of magnets 148.

The magnets 148 can magnetically attract the mounting plate 191 through the rear wall 141 of the case 110. The magnets 148 are arranged to attract the mounting plate 191 when the rear face 141 of the case 110 is placed in abutment with the mounting plate 191. The mounting plate 191 can be released from the magnets 148 by pulling the case 110 away from the mounting plate 191.

The mounting plate 191 is generally rectangular. The mounting plate 191 has rounded corners. The length of the mounting plate 191 is measured along an axis parallel to the height of the case 110. The length may be between about 80 mm and about 120 mm. The width of the mounting plate 191 is measured along an axis parallel to the width of the case 110. The width may be between about 70 mm and about 110 mm. The thickness of the mounting plate 191 is measure along an axis parallel to the depth of the case 110. The thickness may be between about 2 mm and about 6 mm.

The mounting attachment 190 further comprises a plurality of adhesive strips 192. The adhesive strips 192 are arranged on a rear face of the mounting plate 191. The adhesive strips 192 are adhered to the mounting plate 191. One side of the adhesive strips is attached to the mounting plate 191, the other side can be adhered to a surface. The adhesive strips 192 may be formed from an adhesive sheet material configured to adhere on both surfaces. For example, the adhesive strips 192 may be formed from double sided adhesive tape or foam pads. Alternatively, the adhesive strips 192 may be pre-formed strips or dots of pressure sensitive adhesive.

The mounting attachment 190 can be fixed to a surface by the adhesive strips 192. The case 110 can be releasable attached to the surface by magnetically attaching to the mounting attachment 190.

The mounting attachment 190 comprises four adhesive strips 192. The adhesive strips 192 may be between about 5 mm and about 15 mm wide. The adhesive strips 192 may be between about 10 mm and about 20 mm long. The adhesive strips 192 are arranged in a square formation. The adhesive strips 192 are located at the four corners of the mounting plate 191. The adhesive strips 192 are positioned 5 mm from the edge of the mounting plate.

The packaging assembly 100 can be mounted on any surface using the mounting attachment 190. The packaging assembly 100 can be mounted in a household fridge. The packaging assembly 100 may be mounted on a side wall of the fridge, the roof of the fridge, on the underside of a shelf or the inside of the fridge door. The packaging assembly 100 may be mounted in a location which is prominent and cannot be hidden by food and the like when the fridge is full. The packaging assembly 100 may be mounted in a location where it is separated from food in the fridge.

When the mounting attachment 190 is positioned, the case 110 may be freely attached to and detached from the mounting attachment 190. The case 110 may be detached from the mounting attachment 190 and removed from the fridge, leaving the mounting attachment 190 in position. The case 110 may be detached and removed from the fridge so that the user can operate the lid 120 and extract an injection device 10 in comfort, without reaching into the fridge. The case 110 may be removed from the fridge to easily refill the case 110 with new injection devices 10. The case 110 may be removed from the fridge to easily clean the case 110.

Figure 3:
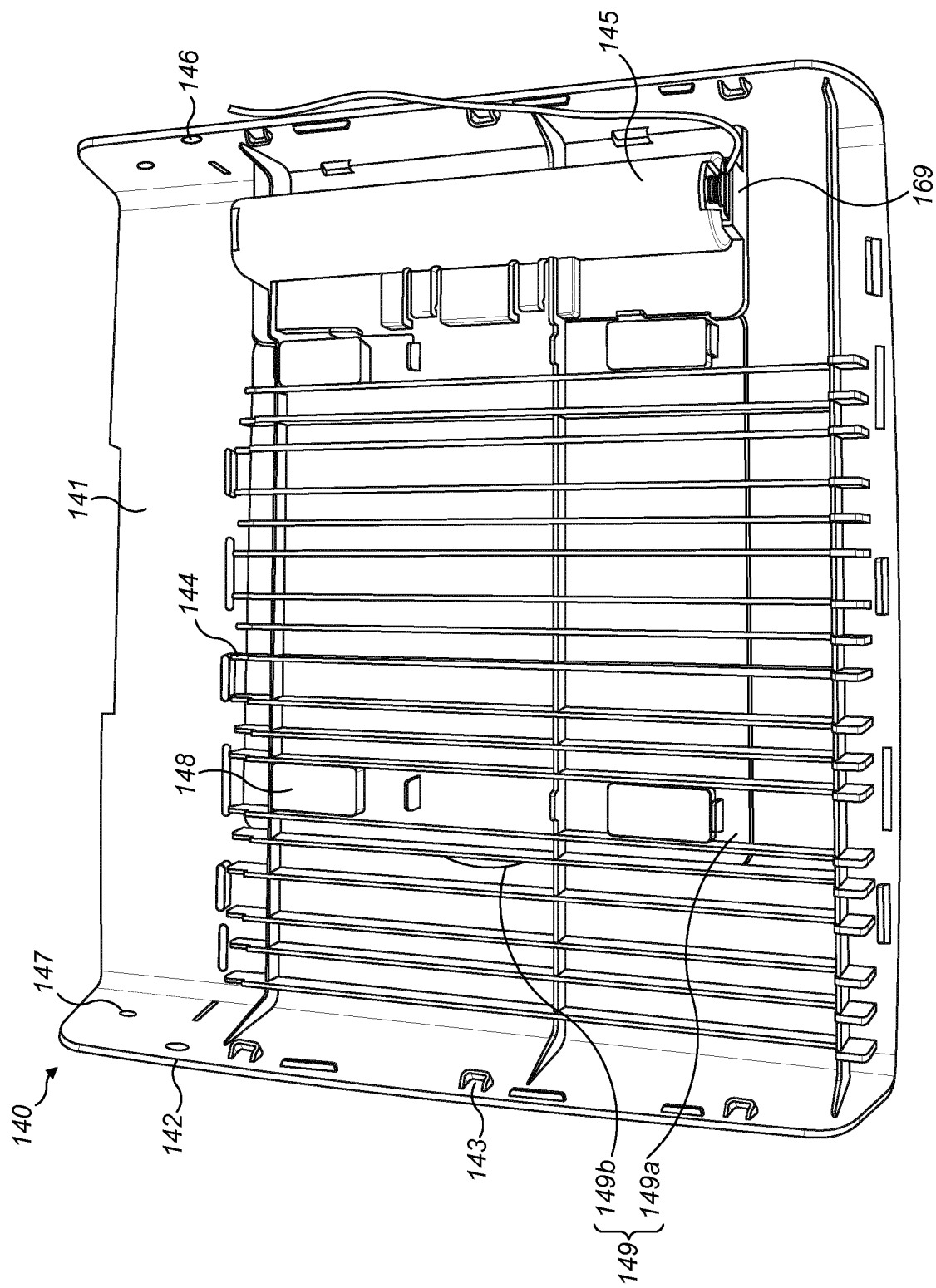
FIG. 3 is an isometric view of the packaging assembly of FIG. 1.

With further reference to FIG. 3, the second part 140 of the packaging assembly 100 is shown. The second part 140 comprises the rear wall 141 and side walls 142 of the case 110. The second part 140 of the case 110 is formed from a single piece. Each of the side walls 142 the second part 140 comprises a plurality of engaging hooks 143 for engaging with the first part 130. The engaging hooks 143 are each configured to engage with the corresponding opening 133 in the first part 130 of the case 110. Three openings 133 are formed along each edge of the first part 130. Each of the side walls 142 comprises three engaging hooks 143. The engaging hooks 143 are arranged on an inner face of the respective side wall.

Each of the side walls 142 comprises a second hinging part 146 configured to engage with the first hinging part 126. The first hinging part 126 and the second hinging part 146 together form a hinge for attaching the lid 120 to the second part 140 of the case 110. For example, the second hinging part 146 comprises an opening configured to receive the protruding part of the first hinging part 126. The first hinging part 126 is configured to rotate within the opening of the second hinging part 146. The lid 120 is attached in a hinged manner between the second hinging parts 146 of the side walls 142.

Each of the side walls 142 comprises a second latching part 147 configured to engage with the first latching part 127 of the lid 120. The first latching part 127 is configured to releasably engage with the second latching part 147 to maintain the lid 120 in a closed position. For example, the second latching part 147 comprises an opening to receive the protruding part of the first latching part 127. The first latching part 127 is configured to releasably engage with the opening of the second latching part 147.

The second part 140 is formed having a recessed area 149 in the rear wall 141. The recessed area 149 is recessed with respect to the flat external surface of the rear wall 141. The recessed area 149 is configured to receive the mounting plate 191.

The recessed area 149 comprises a first area 149*a* and a second area 149*b*. The first area 149*a* is configured to receive the mounting plate 191. The second area 149*b* can be used to grasp an edge of the mounting plate 191, or to reach beneath the mounting plate 191, to lever the mounting attachment 190 out of the recessed area 149 against the pull of the magnets 148.

The depth of the recessed area 149 corresponds to the thickness of the mounting plate 191. A height and a width of the first area 149a correspond respectively to the height and width of the mounting plate 191.

The second area 149b is adjacent to the first area 149a. The second area 149b extends from a long edge of the first area 149a, which lies parallel to the side walls 142 of the case 110. The second area 149b may be arranged adjacent to either of the long edges of the first area 149a. The second area 149b is generally rectangular. The second area 149b is centred with respect to the height of the first area 149b.

A height of the second area 149b, being parallel to the height of the first area 149a, may be about 40 mm to about 60 mm. A width of the second area 149b, being parallel to the width of the first area 149a, may be about 5 mm to about 20 mm. A depth of the second area 149b may be greater than the depth of the first area 149a. The depth of the second area 149b may be up to about 10 mm.

The second part 140 further comprises a plurality of guide rails 144 for holding and storing the plurality of injection devices in position within the case 110. The guide rails 144 are internal walls which extend along the length of the case 110 from the openings 151 to the base of the second part 140. Three guide rails 144 are provided for each of the openings 151. For each set of three guide rails 144, the two outer rails are taller than the central rail. The guide rails 144 of the second part 140 are aligned with the guide rails 134 of the first part 130. The guide rails 134 and guide rails 144 for each opening 151 form a roughly circular channel to hold each injection device in position.

The guide rails 144 of the second part 140 are further configured to hold the plurality of magnets 148 in position. Each of the magnets 148 is held securely between two adjacent guide rails 144. Further internal walls extending perpendicular to the guide rails 144 may be provided to hold the magnets 148 in position. The magnets 148 are positioned on the internal side of the rear face 141.

The magnets 148 are aligned with the recessed area 149. The magnets 148 are located in alignment with the four corners of the first area 149a. The magnets 148 may be aligned with a position which is 5 mm from each edge of the first area 149a. The magnets 148 are configured to attract the mounting plate 191 through the rear face 141 of the second part 140 when the mounting attachment 190 is positioned in the recessed area 149.

The second part 140 of the case 110 further comprises a battery compartment 145 formed in the rear face 141. The battery compartment 145 is a recess configured to receive the plurality of batteries 170. The battery compartment 145 is open and accessible through the rear side of the case 110. The battery contact 169 is arranged within the battery compartment 145.

Figure 4:
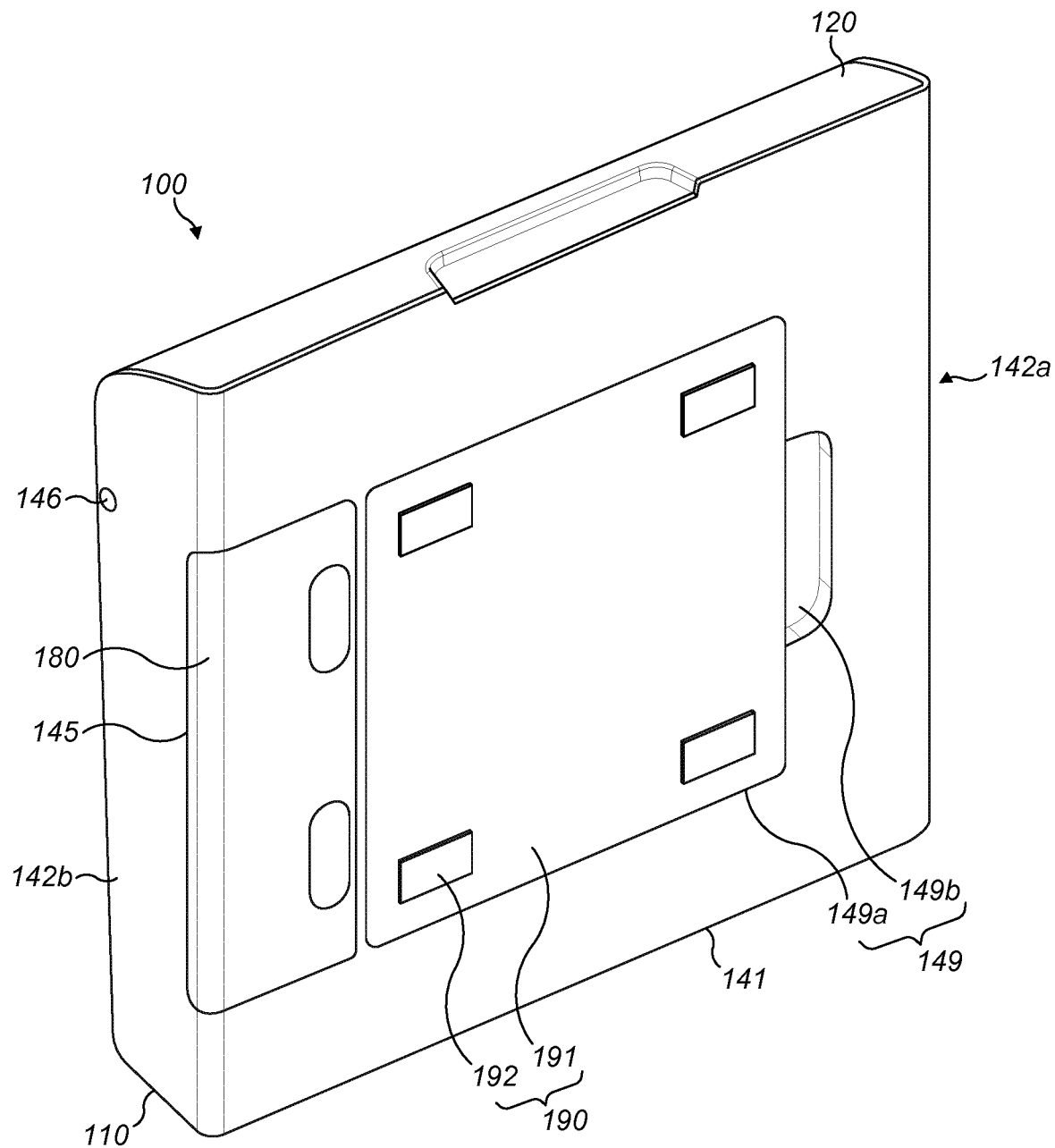
FIG. 4 is an exploded view of the packaging assembly of FIG. 1.

With further reference to FIG. 4, an isometric rear view of the packaging assembly 100 is shown.

The packaging assembly 100 further comprises a battery cover 180 configured to slidably engage with the battery compartment 145 of the second part 140. The battery cover is configured to cover the battery compartment 145 when the packaging assembly 100 is in use. The battery cover 180 may comprise a latch (not shown) to engage with the second part 140 of the case 110 and to retain the battery cover 180 in position.

The mounting attachment 190 is shown in position in the recessed area 149 in FIG. 4. A rear face of the mounting plate 191 lies flush with the external face of the rear wall 141 when the mounting attachment 190 is placed in the recessed area 149. When the mounting attachment 190 is placed in the recessed area 149 the plurality of magnets 148 are configured to attract the mounting plate 191 to hold the mounting attachment 190 in position.

The recessed area 149 allows the case 110 to lie flat against a surface when the mounting attachment 190 is attached to the surface. The recessed area 149 is configured to fit tightly over the mounting plate 191 to prevent the case 110 from turning. The recessed area 149 can prevent the case 110 from turning if knocked unintentionally, and can prevent the case 110 from being unintentionally released from the mounting attachment 190.

Figure 5:
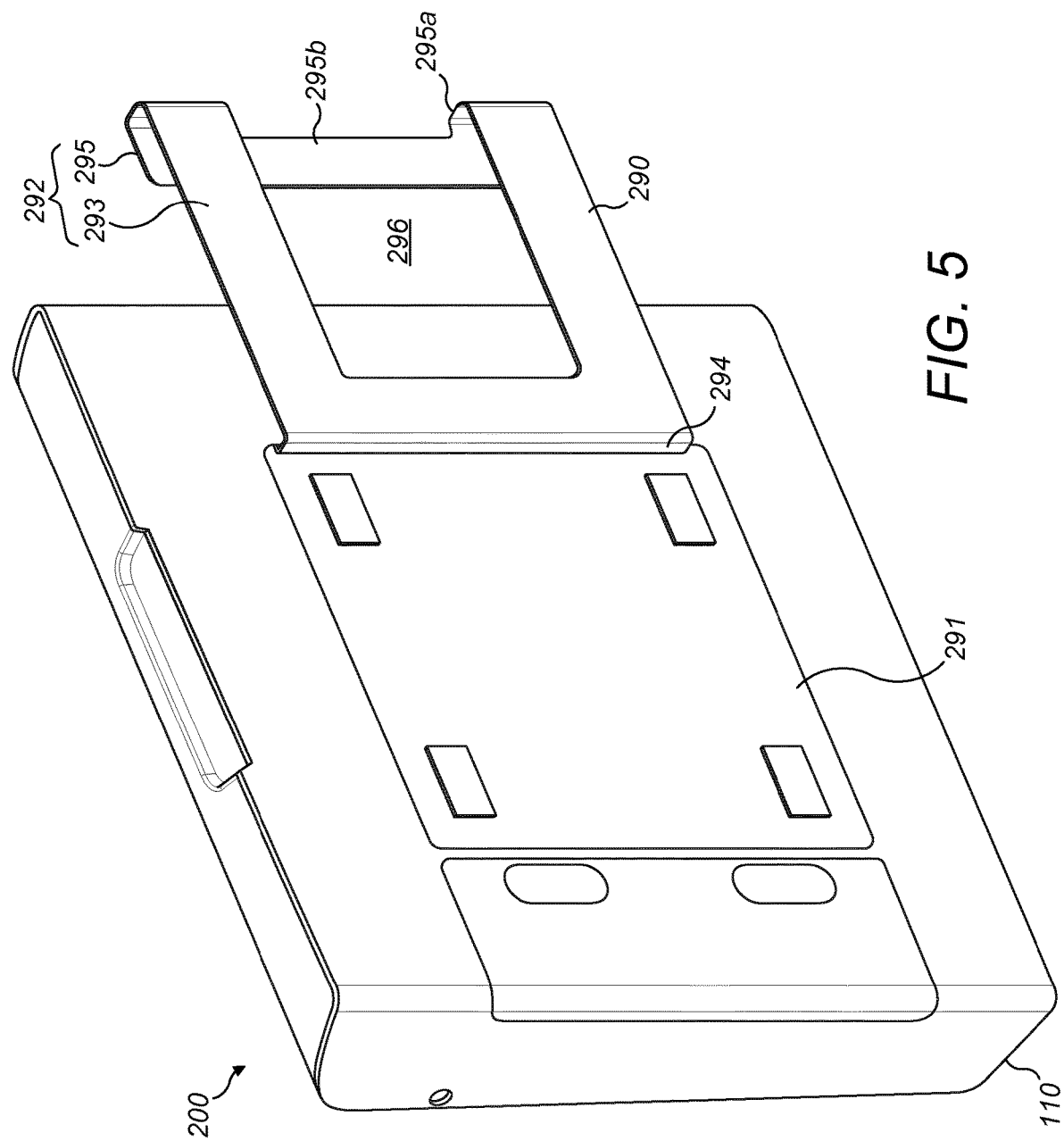
FIG. 5 is an isometric view of a packaging assembly according to an exemplary embodiment.

With respect to FIG. 5, a packaging assembly 200 according to a second embodiment is shown. Elements which are different to those of the first embodiment will be described, and the same reference numerals are used to refer to features common to both embodiments.

The packaging assembly 200 comprises a case 110, as described above with respect to the first embodiment, and a mounting attachment 290. The mounting attachment 290 comprises a mounting plate 291 and a hanger arrangement 292. The hanger arrangement 292 is configured to hang the packaging assembly 200 from a supporting object. The hanger arrangement 292 can be positioned in a hanging fashion and the case 110 can be coupled with the mounting plate 291.

The mounting plate 291 is a metal plate, substantially as described with respect to the mounting plate 191 of the first embodiment. The mounting plate 291 is a suitable size to be received by the recessed area 149.

The hanger arrangement 292 comprises an extending part 293 and a hook 295. When the mounting attachment 290 is attached to the case 110, the extending part 293 is arranged to extend away from the body of the case 110. The hook 295 is arranged at an end of the extending part 293 furthest from the case 110. The hook 295 is configured to fit over a supporting body. The case 110 hangs directly below the hook 295 at a lower end of the extending part 293.

The extending part 293 extends from the case 110 substantially in the same plane as the rear wall 141. The extending part 293 may extend along a plane which is adjacent to the external face of the rear wall 141.

The extending part 293 is attached to a rear face of the mounting plate 291. The extending part 293 extends away from the mounting plate 291 substantially in the same plane as the rear face of the mounting plate 291. The extending part 293 extends in a sideways direction away from the mounting plate 291, where sideways is with respect to the side walls 142 of the case 110 when the mounting attachment 290 is disposed in the recessed area 149. Where the mounting plate 291 is a rectangular shape, the extending part 292 extends away from a long edge of the mounting plate 291.

When the hanger arrangement 292 is hanging from a supporting object, the extending part 293 extends upwards. The case 110 can be coupled to the mounting plate 291 with one of the side walls 142 facing upwards.

The extending part 293 is a rectangular shape. The length of the extending part 293, which is measured along an axis parallel to the width of the mounting plate 291, may be between about 80 mm and about 100 mm. The height of the extending part 293, which is measured parallel to the height of the mounting plate 291, may be between about 80 mm and about 120 mm. The height of the extending part 293 may be shorter than the length of the mounting plate 291 by about 5 mm. The extending part 293 is formed from a sheet of metal. The thickness of the sheet of material is between about 1 mm and about 3 mm.

The extending part 293 is joined to the rear face of the mounting plate 291 close to the long edge of the mounting plate 291. A side edge of the extending part 293 is attached to the rear face of the mounting plate 291. The side edge of the extending part 293 extends parallel to the long edge of the mounting plate 291.

A joining portion 294 displaces the extending part 293 in a rearwards direction, such that the extending part 293 extends adjacent to the rear wall 141 of the case 110. The joining portion 294 comprises an end portion of the extending part 293 nearest to the mounting plate 291. The joining portion 294 is deflected through a right angle towards the rear face of the mounting plate 291. The side edge of the extending part 293 is curved to face the rear face of the mounting plate 291, and is attached thereto.

The extending part 293 is formed to extend a short distance in a direction perpendicular to the rear face of the mounting plate 291, then is deflected through a right angle to extend along to the full length of the extending part 293 along a plane which is adjacent to the rear face. The joining portion 294 may extend in a direction perpendicular to the rear face of the mounting plate for between about 1 mm and about 5 mm.

The joining portion 294 may be deflected to form a square corner. Alternatively, the joining portion 294 may be rounded. The extending part 293 may be bent or folded to form the joining portion 294. Alternatively, a second piece of material may be attached to the extending portion 294 at a right angle by, for example, welding or bonding.

The extending part 293 of the hanger arrangement 292 is attached to the mounting plate 291 by welding or bonding. Alternatively, the joining portion 294 may extend through a slot formed in the mounting plate 291. The joining portion 294 may be retained in the slot by a shrink fitting process or similar. Further alternatively, the hanger arrangement 292 and mounting plate 291 may be formed from a single piece by casting or machining.

The hook 295 extends from an end of the extending part 293 which is furthest from the mounting plate 291. The hook 295 is configured to engage with a supporting object. The hook 295 is shaped to fit over a supporting object such that the extending part 293 of the hanger arrangement 292 hangs beneath the supporting object.

With respect to the extending part 293, the hook 295 extends out of the plane in a direction towards the mounting plate 291. That is, the hook 295 is disposed towards the case 110 when the mounting attachment 290 is attached to the case 110. The hanger arrangement 292 is configured to support the case 110 directly below the hook 295, when the hook 295 is hanging from a supporting object.

The hook 295 comprises a first part 295a and a second part 295b. The first part 295a extends from the end of the extending part 293. The first part 295a extends perpendicular to the extending part 293. The first part 295a extends in a forward direction from the extending part 293. That is, the first part 295a extends in the same direction as the joining portion 294, towards the mounting plate 291.

The second part 295b extends from an end of the first part 295a which is furthest from the extending part 293. The second part 295b extends perpendicular to the first part 295a. The second part 295b extends in a sideways direction from the first part 295a. That is, the second part 295b extends along an axis which is parallel to the extending part 293. The second part 295b extends towards the mounting plate 291.

The length of the first part 295a may be between about 10 mm and about 20 mm. The length of the second part 295b may be between about 15 mm and about 35 mm. The hanger arrangement 292 may be deflected to form the hook 295. The hook 295 may be formed having square corners where deflected. Alternatively, the hook 295 may be rounded. The hanger arrangement 292 may be bent or folded to form the hook 295. Alternatively, a second piece of material may be attached to the extending portion 294 at a right angle to form the first part 295a, and a third piece of material may be attached to the first part 295a to form the second part 295b.

The hanger arrangement 292 further comprises a cut-out 296. The cut-out 296 is a removed or absent portion of material in the hanger arrangement 292. The cut-out 296 reduces the weight of the hanger arrangement 292. The cut-out 296 may be removed from the hanger arrangement 292 after forming the hanger arrangement 292. Alternatively, the hanger arrangement 292 may be formed with the cut-out 296 in place.

The cut-out 296 extends over a portion of the extending part 293, the first part 295a of the hook 295 and the second part 295b of the hook 295. The shape of the cut-out 296 is generally rectangular, and follows the deflected form of the hook 295. The corners of the cut-out 296 may be rounded. The length of the cut-out 296, as measured along the length of the extending part 293 and along the path of the hook 295, may be between about 80 mm and about 100 mm. The height of the cut-out 296, as measured along the height of the extending part 293, may be between about 60 mm and about 90 mm.

The cut-out 296 is arranged centrally with respect to the height of the hanger arrangement 292. A portion of the hanger arrangement 292 between about 10 mm and about 30 mm remains above and below the cut-out 296. The cut-out 296 extends over a portion of the length of the extending part 293. A side edge of the cut-out 296 which is closest to the mounting plate 291 is arranged between about 10 mm and about 30 mm from the side edge of the extending part 293.

The cut-out 296 extends from the side edge along the entire length of the extending part 293. The cut-out 296 extends from the end of the extending part 293 along a full length of the first part 295a. The cut-out 296 extends from the end of the first part 295a along a portion of the length of the second part 295b. A side edge of the cut-out 296 which is closest to the end of the second part 295b is arranged between about 10 mm and about 20 mm from the end of the second part 295b.

The mounting attachment 290 allows the case 110 of the packaging assembly 200 to be hung inside a household fridge. In particular, the mounting attachment 290 can be hung from a door shelf of the fridge. A typical fridge door shelf is a tray shape having four vertical walls and a base. The tray is mounted on horizontal rails formed in the internal face of the fridge door and can be slidably removed in a direction perpendicular to the internal face. The hook 295 can be placed over the rear wall of the tray which faces the internal face of the fridge door when the tray is mounted thereon.

The extending part 293 hangs down from the rear wall of the fridge door shelf. The extending part 293 lies flat against the internal face of the fridge door. The mounting plate 291 faces away from the fridge door towards an interior of the fridge. The case 110 may be attached to the mounting plate 191 in position against the internal face of the fridge door.

The rear wall 141 of the case 110, the extending part 293 of the mounting attachment 290, and the internal face of the fridge door lie substantially in the same plane, directly adjacent to each other.

The packaging arrangement 20 can be located in a prominent position on the internal face of the fridge door. The packaging arrangement is located away from food and the like in the fridge. The packaging arrangement is unlikely to be covered or knocked in this location.

The extending part 293 extends sideways with respect to the case 110, such that the case 110 is arranged with one of the side walls 142 facing upwards when mounted in the fridge door. The lid 120 of the packaging arrangement 20 faces sideways with respect to the fridge door. The lid 120 faces the patient when the fridge door is opened and the display 161 can be seen through the viewing window 121.

The mounting plate 291 and recess 149 are symmetrical such that the lid 120 can face to either side, according to which side the fridge door is hinged. The recessed area 149 is configured to fit tightly over the mounting plate 291 to prevent the case 110 from turning. The recessed area 149 can prevent the case 110 from turning if knocked unintentionally, and can prevent the case 110 from being unintentionally released from the mounting attachment 290.

Figure 6:
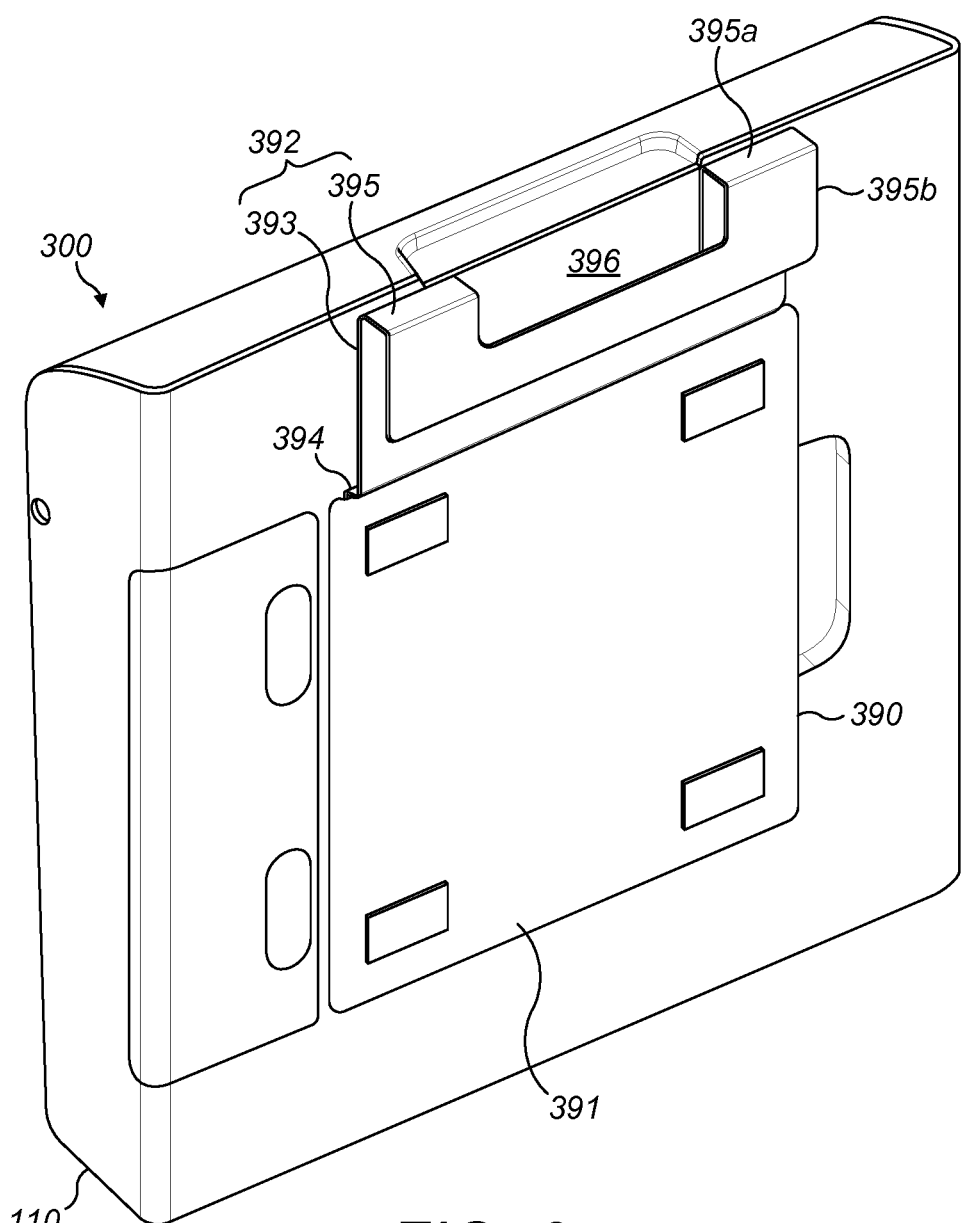
FIG. 6 is an isometric view of a packaging assembly according to an exemplary embodiment.

With respect to FIG. 6, a packaging assembly 300 according to a third embodiment is shown. Elements which are different to those of the first embodiment will be described, and the same reference numerals are used to refer to features common to both embodiments.

The packaging assembly 300 comprises a case 110, as described above with respect to the first embodiment, and a mounting attachment 390. The mounting attachment 390 comprises a mounting plate 391 and a hanger arrangement 392. The hanger arrangement 392 is configured to hang the packaging assembly 300 from a supporting object. The hanger arrangement 392 can be positioned in a hanging fashion and the case 110 can be coupled with the mounting plate 391.

The mounting plate 391 is a metal plate, substantially as described with respect to the mounting plate 191 of the first embodiment. The mounting plate 391 is a suitable size to be received by the recessed area 149.

The hanger arrangement 392 comprises an extending part 393 and a hook 395. When the mounting attachment 390 is attached to the case 110, extending part 293 is arranged to extend away from the body of the case 110. The hook 395 is arranged at an end of the extending part 393 furthest from the case 110. The hook 395 is configured to fit over a supporting body. The case 110 hangs at a lower end of the extending part 393. The case 110 hangs on the opposite face of the extending part 393 to the hook 395.

The extending part 393 extends from the case 110 substantially in the same plane as the rear wall 141. The extending part 393 may extend along a plane which is adjacent to the external face of the rear wall 141.

The extending part 393 is attached to the rear face of the mounting plate 391. The extending part 393 extends away from the mounting plate 391 substantially in the same plane as the rear face of the mounting plate 391. The extending part 393 extends in an upwards direction away from the mounting plate 391, where upwards indicates along the axis on which the height of the mounting plate 391 is measured. Where the mounting plate 391 is a rectangular shape, the extending part 392 extends away from a short edge of the mounting plate 391.

When the hanger arrangement 392 is hanging from a supporting object, the extending part 393 extends upwards. The case 110 can be coupled to the mounting plate 391 with the lid 120 facing upwards.

The extending part 393 is a rectangular shape. The length of the extending part 393, which is measured along an axis parallel to the height of the mounting plate 391, may be between about 30 mm to about 50 mm. The width of the extending part 393, which is measured parallel to the width of the mounting plate 391, may be between about 60 mm to about 90 mm. The width of the extending part 393 may be shorter than the length of the mounting plate 391 by about 5 mm. The extending part 393 is formed from a sheet of metal. The thickness of the sheet of material is between about 1 mm and about 3 mm.

The extending part 393 is joined to the rear face of the mounting plate 391 close to the short edge of the mounting plate 391. A lower edge of the extending part 393 is attached to the rear face of the mounting plate 391. The lower edge of the extending part 393 extends parallel to the top edge of the mounting plate 391.

A joining portion 394 displaces the extending part 393 in a rearwards direction, such that the extending part 393 extends adjacent to the rear wall 141 of the case 110. The joining portion 394 comprises an end portion of the extending part 393 nearest to the mounting plate 391. The joining portion 394 is deflected through a right angle towards the rear face of the mounting plate 391. The lower edge of the extending part 393 is curved to face the rear face of the mounting plate 391, and is attached thereto.

The extending part 393 is formed to extend a short distance in a direction perpendicular to the rear face of the mounting plate 391, then is deflected through a right angle to extend along to the full length of the extending part 393 in a direction parallel to the rear face. The joining portion 394 may extend in a direction perpendicular to the rear face of the mounting plate for between about 1 mm and about 5 mm.

The joining portion 394 may be deflected to form a square corner. Alternatively, the joining portion 394 may be rounded. The extending part 393 may be bent or folded to form the joining portion 394. Alternatively, a second piece of material may be attached to the extending portion 394 at a right angle by, for example, welding or bonding.

The extending part 393 of the hanger arrangement 392 is attached to the mounting plate 391 by welding or bonding. Alternatively, the joining portion 394 may extend through a slot formed in the mounting plate 391. The joining portion 394 may be retained in the slot by a shrink fitting process or similar. Further alternatively, the hanger arrangement 392 and mounting plate 391 may be formed from a single piece by casting or machining.

The hook 395 extends from an end of the extending part 393 which is furthest from the mounting plate 391. The hook 395 is configured to engage with a supporting object. The hook 395 is shaped to fit over a supporting object such that the extending part 393 of the hanger arrangement 392 hangs beneath the supporting object.

With respect to the extending part 393, the hook 395 extends out of the plane in a direction away from the mounting plate 391. That is, the hook 395 is disposed away from the case 110 when the mounting attachment 390 is attached to the case 110. The hanger arrangement 392 is configured to support the case 110 on the opposite side of the extending part 393 to the hook 395, when the hook 395 is hanging from a supporting object.

The hook 395 comprises a first part 395a and a second part 395b. The first part 395a extends from the end of the extending part 393. The first part 395a extends perpendicular to the extending part 393. The first part 395a extends in a rearwards direction from the extending part 393. That is, the first part 395a extends along an axis perpendicular to the rear face of the mounting plate 391, in a direction away from the mounting plate 391

The second part 395b extends from an end of the first part 395a which is furthest from the extending part 393. The second part 395b extends perpendicular to the first part 395a. The second part 395b extends in a downwards direction from the first part 395a. That is, the second part 395b extends along an axis which is parallel to the extending part 393. The second part 395b extends towards the mounting plate 391.

The length of the first part 395a may be between about 10 mm and about 20 mm. The length of the second part 395b may be between about 15 mm and about 35 mm. The hanger arrangement 392 may be deflected to form the hook 395. The hook 395 may be formed having square corners where deflected. Alternatively, the hook 395 may be rounded. The hanger arrangement 392 may be bent or folded to form the hook 395. Alternatively, a second piece of material may be attached to the extending portion 394 at a right angle to form the first part 395a, and a third piece of material may be attached to the first part 395a to form the second part 395b.

The hanger arrangement 392 further comprises a cut-out 396. The cut-out 396 is a removed or absent portion of material in the hanger arrangement 392. The cut-out 296 reduces the weight of the hanger arrangement 392. The cut-out 396 may be removed from the hanger arrangement 392 after forming the hanger arrangement 392. Alternatively, the hanger arrangement 392 may be formed with the cut-out 396 in place.

The cut-out 396 extends over a portion of the extending part 393, the first part 395a of the hook 395 and the second part 395b of the hook 395. The shape of the cut-out 396 is generally rectangular, and follows the deflected form of the hook 395. The corners of the cut-out 396 may be rounded. The length of the cut-out 396, as measured along the length of the extending part 393 and along the path of the hook 395, may be between about 40 mm and about 50 mm. The width of the cut-out 396, as measured along the width of the extending part 393, may be between about 40 mm and about 75 mm.

The cut-out 396 is arranged centrally with respect to the width of the hanger arrangement 392. A portion of the hanger arrangement 392 between about 15 mm and about 35 mm remains to either side of the cut-out 396. The cut-out 396 extends over a portion of the length of the extending part 393. A lower edge of the cut-out 396 which is closest to the mounting plate 391 is arranged between about 10 mm and about 30 mm from the lower edge of the extending part 393.

The cut-out 396 extends from the lower edge along the entire length of the extending part 393. The cut-out 396 extends from the end of the extending part 393 along a full length of the first part 395a. The cut-out 396 extends from the end of the first part 395a along a portion of the length of the second part 395b. An edge of the cut-out 396 which is closest to the end of the second part 395b is arranged between about 5 mm and about 20 mm from the end of the second part 395b.

The mounting attachment 390 allows the case 110 to be hung in position in a household fridge. In particular, the mounting attachment 390 can be hung inside a box within the fridge. A typical household fridge includes one or more boxes for holding fruit and vegetables and the like. The boxes have four walls and a base and can be slid into position beneath or between the shelves of the fridge. The hook 395 can be placed over a wall of a box such that the hanger arrangement 392 hangs down from the hook inside the box.

The hanger arrangement 293 supports the mounting plate 391 inside position against an internal wall of the box. The case 110 may be attached to the mounting plate 391 within the box. The rear wall 141 of the case 110, the extending part 393 of the mounting attachment 390, and the internal wall of the box lie substantially in the same plane, directly adjacent to each other.

The case 110 can be attached in a vertical configuration with the lid 120 facing upwards. The lid 120 faces the patient when the patient looks into the top of the box. The display 161 can be seen through the viewing window 121.

With respect to FIG. 7, a kit 400 for providing a packaging assembly (100,200,300) is provided. The kit comprises a case 110, substantially as described with respect to the first embodiment.

The kit 400 comprises a plurality of mounting attachments 190,290,390 configured to be attached to the case 110. One of the plurality of mounting attachments 190,290,390 can be attached to the case 110 to form the packaging assembly 100,200,300. The case 110 may be mounted in a variety of locations and positions according the mounting attachment 190,290,390.

The kit 400 comprises a first mounting attachment 190, substantially as described with respect to the first embodiment. The first mounting attachment 190 can be attached to the case 110 to form the packaging assembly 100 according to the first embodiment.

The kit 400 further comprises a second mounting attachment 290, substantially as described with respect to the second embodiment. The second mounting attachment 290 can be attached to the case 110 to form the packaging assembly 200 according to the second embodiment.

The kit 400 further comprises a third mounting attachment 390, substantially as described with respect to the third embodiment. The third mounting attachment 390 can be attached to the case 110 to form the packaging assembly 300 according to the third embodiment.

The case 110 of the kit 400 can be attached to any one of the provided mounting attachments 190,290,390. The case 110 can be mounted to any flat surface using the first mounting attachment 190. The case 110 can be mounted in a hanging position from the internal shelf of a fridge door using the second mounting attachment 290. The case 110 can be mounted in a hanging position inside a box in fridge, using the third mounting attachment 390.

Using the kit 400, the case 110 may be conveniently moved to a different position by detaching the case 110 from one mounting attachment, and attaching the case 110 to another of the plurality of mounting attachments.

In some embodiments, an exemplary injection device is configured to inject a medicament into a user's body. The injection device includes a housing which typically contains a reservoir containing the medicament to be injected (e.g., a syringe) and the components required to facilitate one or more steps of the delivery process. The injection device can also include a cap assembly that can be detachably mounted to the housing. Typically a user must remove the cap from the housing before the injection device can be operated.

In some embodiments, the housing is substantially cylindrical and has a substantially constant diameter along the longitudinal axis. The housing has a distal region and a proximal region. The term "distal" refers to a location that is relatively closer to a site of injection, and the term "proximal" refers to a location that is relatively further away from the injection site.

In some embodiments, the injection device can also include a needle sleeve coupled to the housing to permit movement of the sleeve relative to the housing. For example, the sleeve can move in a longitudinal direction parallel to longitudinal axis X. Specifically, movement of the sleeve in a proximal direction can permit a needle to extend from the distal region of the housing.

Insertion of the needle can occur via several mechanisms. For example, the needle may be fixedly located relative to the housing and initially be located within an extended needle sleeve. Proximal movement of the sleeve by placing a distal end of the sleeve against a user's body and moving the housing in a distal direction will uncover the distal end of the needle. Such relative movement allows the distal end of the needle to extend into the user's body. Such insertion is termed "manual" insertion as the needle is manually inserted via the user's manual movement of the housing relative to the sleeve.

Another form of insertion is "automated," whereby the needle moves relative to the housing. Such insertion can be triggered by movement of the sleeve or by another form of activation, such as, for example, a button. In some embodiments, the button is located at a proximal end of the housing. However, in other embodiments, the button could be located on a side of the housing.

Other manual or automated features can include drug injection or needle retraction, or both. Injection is the process by which a bung or a piston is moved from a proximal location within a syringe to a more distal location within the syringe in order to force a medicament from the syringe through the needle. In some embodiments, a drive spring is under compression before the device is activated. A proximal end of the drive spring can be fixed within the proximal region of the housing, and a distal end of the drive spring can be configured to apply a compressive force to a proximal surface of the piston. Following activation, at least part of the energy stored in the drive spring can be applied to the proximal surface of the piston. This compressive force can act on the piston to move it in a distal direction. Such distal movement acts to compress the liquid medicament within the syringe, forcing it out of the needle.

In some embodiments, following injection, the needle can be retracted within the sleeve or the housing. Retraction can occur when the sleeve moves distally as a user removes the device from a user's body. This can occur as the needle remains fixedly located relative to the housing. Once a distal end of the sleeve has moved past a distal end of the needle, and the needle is covered, the sleeve can be locked. Such locking can include locking any proximal movement of the sleeve relative to the housing.

Another form of needle retraction can occur if the needle is moved relative to the housing. Such movement can occur if the syringe within the housing is moved in a proximal direction relative to the housing. This proximal movement can be achieved by using a retraction spring, located in the distal region. A compressed retraction spring, when activated, can supply sufficient force to the syringe to move it in a proximal direction. Following sufficient retraction, any relative movement between the needle and the housing can be locked with a locking mechanism. In addition, the button or other components of the device can be locked as required.

It will be appreciated that the above described embodiments are purely illustrative and are not limiting on the scope of the claims. Other variations and modifications will be apparent to persons skilled in the art upon reading the present application, and some will now be described.

The case of the packaging arrangement may be a generally rectangular shape or may be any other shape suitable for containing the plurality of injectors. The case may be a suitable shape and size for placement within a household refrigerator.

The case may be formed to enclose the injectors and may be sealed. Alternatively, the case may be formed as a structure for supporting the plurality of injection devices externally. The injectors may be arranged in one or more rows, e.g. a row of six or two rows of three, or in a circular arrangement. The injectors may be arranged to hang below a supporting structure.

The case may be configured to store any number of injection devices, according to the dosage requirements of the medicament. For example, the case may store between 5 and 15 injection devices. Case may be sized to store enough injection devices for one quarter, or for a 6 month period. Where medicament is administered more regularly, the case may store enough injectors for one week.

The case may be formed of an opaque material. One or more of the components of the case may be formed with at least a transparent portion. A transparent portion of the case may allow the user to see the number of injection devices, or to see the user interface. One or more components of the case may be translucent to improve visibility of a visual reminder output.

The case may be formed of a plastics material such as polyethylene, polystyrene, polycarbonate, or it may be made of any other suitable material. Desired properties for the material of the case include temperature stability, moderate impact strength, resistance to cleaning fluids, a wipe-clean finish, and rigidity.

Each part of the case may be formed in a single piece e.g. a moulded plastic part. Alternatively, parts may be machined. The body of the case may be formed from two parts joined or attached together, or may be formed in a single part. An internal of the case may be formed as a single large cavity, a cavity divided into a plurality of areas for holding each injector, or may be formed as a plurality of cavities for individually holding each injector.

The hanger arrangement may be attached to the case. For example, the hanger arrangement may be formed with the second part in a single piece. The hanger arrangement may extend from the rear wall of the case. Alternatively, the hanger arrangement may extend from the top of the case or the side of the case, substantially in the plane of the rear wall.

The hanger arrangement may include any suitable form of hook attachment which can support the case. The hook may be rounded or may be an L-shape. The hook of the hanger arrangement may be biased inwards to grip a supporting object. The extending part may be longer or shorter to support the case in a different position. The extending part may have an adjustable length. The hanger arrangement may comprise a plurality of extending parts and hooks. For example, the hanger arrangement may comprise two parallel extending parts with a hook at the end of each. The extending part may include more than one cut-out section, or may not include a cut-out section.

The hanger arrangement may be formed from any suitable material, for instance, the hanger arrangement may be plastic. Each of the mounting attachments may be formed from plastic and may include one or more magnets to couple with the magnets of the case.

The case may comprise any number of magnets sufficient to support the weight of the packaging arrangement and injection devices. For example, the case may include 2 larger magnets or an arrangement of 6 smaller magnets. The magnets may be any permanent magnets and may be rare earth magnets. The magnets may be formed of neodymium or may be formed of samarium cobalt.

The magnets may be attached to the exterior of the case. The magnets may be mounted on the external face of the rear wall. The magnets may be sited in one or more recesses, to lie flush with the external face of the rear wall of the case. The magnets may be arranged within the boundaries of the recess. The magnets may be arranged to make direct contact with the mounting plate when the mounting plate is disposes in the recess.

Alternatively, the mounting attachment may be coupled to the case with any suitable attachment. For instance, an adhesive layer may attach the mounting attachment to the rear wall of the case. The adhesive may be a pressure sensitive adhesive. Alternatively, a hook and loop fastening material may be used to releasably attach the mounting attachment to the case. The mounting attachment may be formed from a non-magnetic material and attached to the case using adhesive.

Any alternative mounting attachment may be provided alongside one or more other mounting attachments as part of a kit to provide a packaging assembly. The alternative mounting attachment may be provided as part of an alternative kit, or separately to provide additional mounting options in addition to the kit.

The case may further comprise one or more ventilating apertures to allow air flow into the case. Alternatively, the case may be sealed when the lid is in a closed position. The lid may further comprise a rubber seal to prevent air passing into the case between the lid and the case. The case may be insulated to maintain the low temperature of the injectors if removed from the fridge for a short period of time.

The lid may be coupled to the case with a hinge. The mechanism for connecting the lid to the case and for allowing the lid to open and close may take any suitable form. Instead of the hinge mechanism described above, the hinge may be a butt hinge, a living hinge or some other type. The lid may be coupled to the case with a flexible and/or elastic material. The hinge may allow some translational movement as well as pure rotational movement, to allow better viewing of or access to the internal part of the case when the lid is open.

The hinge may allow the removal of the lid by a user. For instance, the protrusions of each of the second hinging parts may be pushed inwards to disengage from the respective first hinging parts and decouple the lid from the case. The user may be provided with one or more alternative lids which may be a different design, for example, a different colour. An alternative lid may have a larger transparent portion or may be entirely opaque.

Alternatively, the lid may slidably engage with the case. The lid may comprise runners at the edges, each configured to engage with a corresponding groove on the case. The lid may slide out of the grooves and decouple from the case. The lid may be arranged to slide to the limit of the grooves and pivot freely in the open position. Further alternatively, the lid may be separate from the case and fixedly attached thereto with a friction fit. The lid may fit tightly within the opening at the upper end of the case, or may fit over an upper portion of the case.

The lid may comprise a latch to maintain the lid in the closed position. The latch may comprise a sliding catch arranged to slidably move between a first position and a second position. The catch may be arranged to protrude from an edge of the lid in the first position. The catch may be configured to slidably retract to not protrude in the second position. The latch may comprise a spring to urge the catch to the first position. The catch may be configured to engage with an opening in the case in the first position when the lid is in the closed position. The catch may engage with the opening to maintain the lid in the closed position.

The latch may be a sprung push-catch push-release mechanism. The latch may be configured to engage with a first push into the closed position and maintain the lid in the closed position. The latch may be configured to disengage with a second push and allow the lid to open. The latch may be configured to engage when the lid is closed to hold the lid in the closed position. The latch may further comprise a release switch to disengage the latch and allow the lid to open. The release switch may be a mechanical switch or an electric switch. The release switch may be an electric switch coupled to a code input, which is configured to disengage the lid catch when a correct code is entered.

The packaging assembly may comprise a case without a lid. The retention mechanism may be arranged at the lower end of the case. The retention mechanism may be arranged to engage with the end of each injector which is passed through the opening. The retention mechanism may comprise a further plurality of openings at the lower end of the case. The further openings may be sized so as to hold the injectors in position with a friction fit. Alternatively, the retention mechanism may comprise a levered pincer arrangement arranged to grip the sides of an injector when the injector is pushed longitudinally into the arrangement, and to release the injector when the injector is pulled longitudinally out of the arrangement.

The retention mechanism may comprise a release switch configured to disengage the retention mechanism. The release switch may be configured to release one or all of the injectors. A plurality of release switches may be provided for the corresponding plurality of injectors. The release switch may be a mechanical switch or lever coupled to the retention mechanism. The release switch may be further coupled to an ejection mechanism. The release switch may be an electromechanical switch.

The ejection mechanism may comprise one or more springs arranged to push a portion of the respective injectors out of the corresponding openings. The ejection mechanism may be biased against the retention mechanism to push each injector when released by the retention mechanism. The retention mechanism may be controlled to release one injector, which is pushed partially out of the opening by the ejection mechanism.

Alternatively, the ejection mechanism may comprise a motorised actuator. For example, a roller arranged perpendicularly to the plurality of injectors may be driven to push the injectors out of the openings. The roller may push all of the injector equally, with the retention mechanism configured to hold all but one of the injectors in position. Further alternatively, the actuator may comprise a protruding part from the base of the case which is driven laterally across the width of the case. The protruding part may be driven along a rail, or may protrude from a belt extending along the width of the case. The protruding part is configured to engage with each injector in turn and push the injector out of the opening.

The display may comprise more than 2 LED arrays, to accommodate larger numbers and messages, or more be a single LED array only. Alternatively, the display may comprise any form of electronic display suitable for displaying a number and/or a message, for example, the display may be an array of LED pixels, an LCD or e-paper screen, or a split-flap display. The display may be arranged in a peripheral module which is separate from the case. The display module may be connected to electrics system with a wired or wireless connection. The electronics system may comprise a display driver which is suitable for chosen display. The display may be configured to provide further status information, or more detail, in the form of text messages on the display.

More than one LED may be included in the user interface to indicate the status of the packaging assembly in more detail. For example, a plurality of LEDs corresponding to the plurality of openings may be provided. Alternatively, a single multi-colour LED may be used. Alternatively, any other form of notification light or visual output transducer may be used in place of the LED.

The speaker may be any suitable form of audio output transducer, for example, an electro-acoustic transducer, a piezoelectric buzzer, a moving diaphragm speaker, or a mechanical bell.

The packaging assembly may include a greater or smaller number of batteries, according to the power requirements of the electronics system. For example, the packaging assembly may include a single battery power pack. The battery or batteries may be removable and replaceable, or may be fixed within the case of the packaging assembly. Alternatively, the packaging assembly may be adapted for a mains power supply, or any alternative power supply.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary). The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A system comprising:
a case configured to hold at least one injection device configured to deliver a medicament; and
a mounting attachment configured to be attached to the case,
wherein the case comprises one or more magnets configured to attach the mounting attachment to the case,
wherein an external face of the case comprises a recess configured to receive at least part of the mounting attachment,
wherein the mounting attachment comprises a rectangular mounting plate and the recess is configured to receive at least part of the rectangular mounting plate when the mounting attachment is attached to the case, and
wherein the mounting attachment comprises a hanger arrangement that extends from the rectangular mounting plate, the hanger arrangement comprising a hook at an end furthest from the rectangular mounting plate.

2. The system of claim 1, wherein the one or more magnets are arranged in an arrangement on an internal face of the case in alignment with the recess.

3. The system of claim 2, wherein the case comprises a plurality of internal walls configured to maintain the arrangement of the one or more magnets, wherein each of the one or more magnets is held between at least two of the plurality of internal walls.

4. The system of claim 1, wherein a depth of the recess is equal to a thickness of the rectangular mounting plate.

5. The system of claim 1, wherein at least a portion of the rectangular mounting plate comprises an adhesive layer.

6. The system of claim 1, wherein the hook is disposed toward the case when the mounting attachment is attached to the case.

7. The system of claim 1, wherein the hook is disposed away from the case when the mounting attachment is attached to the case.

8. A system comprising:
a case configured to hold at least one injection device configured to deliver a medicament; and
a mounting attachment configured to be attached to the case,
wherein the case comprises one or more magnets configured to attach the mounting attachment to the case,
wherein the mounting attachment comprises a hanger arrangement extending from the case substantially in a plane of an external face of the case when the mounting attachment is attached to the case, the hanger arrangement comprising a hook at an end furthest from the case,
wherein the hook is fixed in a position extending out of the plane of the external face of the case and is disposed towards the case when the mounting attachment is attached to the case, and
wherein the mounting attachment comprises a rectangular mounting plate and wherein the hanger arrangement is arranged to extend from the rectangular mounting plate.

9. The system of claim 8, wherein the mounting attachment is formed as part of the case.

10. The system of claim 8, wherein the external face of the case comprises a recess configured to receive at least part of the rectangular mounting plate when the mounting attachment is attached to the case.

11. A kit for providing a packaging assembly, the kit comprising:
a case configured to hold at least one injection device for delivering a medicament, the case comprising one or more magnets configured to attach the case to a mounting attachment;
a first mounting attachment comprising a first mounting plate and a first hanger arrangement, wherein the first hanger arrangement comprises a first hook at a first end furthest from the case, and wherein the first hook is disposed toward the case when the first mounting attachment is attached to the case;
a second mounting attachment comprising a second mounting plate and a second hanger arrangement, wherein the second hanger arrangement comprises a second hook at a second end furthest from the case, and wherein the second hook is disposed away from the case when the second mounting attachment is attached to the case; and
a third mounting attachment comprising a rectangular mounting plate, wherein at least a portion of the rectangular mounting plate comprises an adhesive layer.

12. The kit of claim 11, wherein the case comprises an external face comprising a recess configured to receive at least a part of at least one of the first, second, and third mounting attachments.

13. The kit of claim 12, wherein a depth of the recess is equal to a thickness of the first, second, or third mounting plates.

14. The kit of claim 12, wherein the one or more magnets are arranged in an arrangement on an internal face of the case in alignment with the recess.

15. The kit of claim 14, wherein the case comprises a plurality of internal walls configured to maintain the arrangement of the one or more magnets, wherein each of the one or more magnets is held between at least two of the plurality of internal walls.

* * * * *